United States Patent [19]

Molina

[11] 4,191,048

[45] Mar. 4, 1980

[54] RED-VISIBLE DYE PENETRANT COMPOSITION AND METHOD EMPLOYING SAME

[75] Inventor: Orlando G. Molina, Westminster, Calif.

[73] Assignee: Rockwell International Corporation, El Segundo, Calif.

[21] Appl. No.: 939,551

[22] Filed: Sep. 5, 1978

[51] Int. Cl.² ............................................. G01M 19/00
[52] U.S. Cl. ................................... 73/104; 252/301.19
[58] Field of Search ....................... 252/301.19; 73/104

[56] References Cited

U.S. PATENT DOCUMENTS

| | | | |
|---|---|---|---|
| 3,636,759 | 1/1972 | Alburger | 73/104 |
| 3,915,886 | 10/1975 | Molina | 252/301.19 |
| 4,002,905 | 1/1977 | Molina | 252/301.19 X |
| 4,035,641 | 7/1977 | Molina | 252/301.19 X |

*Primary Examiner*—F. C. Edmundson
*Attorney, Agent, or Firm*—Charles T. Silberberg; L. Lee Humphries; Max Geldin

[57] ABSTRACT

A liquid dye penetrant composition for use in non-destructive testing of objects to locate cracks and other defects or flaws therein, said composition comprising a liquid vehicle, preferably a nonionic surfactant such as an oxyalkylated aliphatic alcohol, and a single phase liquid red azo dye composition consisting essentially of $C_5$–$C_{12}$ alkyl beta naphthols, particularly $C_7H_{15}$ beta naphthols, and containing a liquid organic viscosity depressant compatible with the azo dyes, such as xylene, as represented by the dye composition marketed as Automate Red "B", and which is substantially free of insolubles. The dye penetrant composition may include an extender, preferably an isoparaffinic solvent consisting essentially of a mixture of isoparaffins having a chain length of about 10 to about 17 carbon atoms, and an average chain length of about 13 to about 14 carbon atoms. Such dye penetrant composition is applied to the surface of an object containing cracks and other defects, water is applied to the surface of the object to remove excess liquid dye penetrant composition from the surface without removing such penetrant from the cracks and other defects, and with or without a developer, the surface of the object is viewed under visible light to locate any cracks or other defects in the surface of the body as indicated by brilliant red traces from the dye penetrant remaining in such cracks and other defects.

35 Claims, No Drawings

RED-VISIBLE DYE PENETRANT COMPOSITION AND METHOD EMPLOYING SAME

BACKGROUND OF THE INVENTION

This invention relates to an improved dye penetrant composition and method for non-destructively testing materials to locate defects open to the surface, such as cracks, and is more particularly concerned with the provision of a dye penetrant containing a single phase red liquid azo dye in concentrated form and which is substantially free of insolubles, and provides brilliant red indications of cracks and voids in a part surface when viewed under ordinary light.

In known penetrant inspection methods for rapid location and evaluation of surface flaws such as cracks in test bodies or parts, a dye penetrant composition containing a liquid vehicle and either a fluorescent or daylight visible dye, and which will penetrate the openings of the surface of cracks or other voids in the part, is applied to the surface of the test body, and the excess penetrant composition is removed from the surface of the body. A developer composition may then be applied to the part surface, which acts as a wick and causes the liquid penetrant containing the dye, which was retained in the cracks, to be drawn up out of the surface defects by capillary action. The part is then exposed to appropriate lighting conditions such as invisible fluorescigenous light or white light, depending on the type of dye used, and the location of the surface cracks is revealed by the emission of fluorescent or visible light by the penetrant dye which was retained in the cracks after the penetrant composition was removed from the surface of the part.

For best efficiency, particularly for the detection and location of minute surface cracks, as well as intermediate size and gross cracks, it is necessary that the dye penetrant composition have high brightness and sensitivity.

There are only a relatively small number of commercially available dyes which can be effectively employed in dye penetrant compositions. The dyes employed, including fluorescent and daylight visible dyes, particularly red visible dyes, are powders which are mixed with the liquid vehicle, which can include surfactants or wetting agents, oils, couplers and extender solvents such as hydrocarbons, e.g. kerosene, light fuel oils, and the like, to produce the dye penetrant formulation. While some fluorescent dyes dissolve relatively well in such liquid vehicles, daylight visible red dyes, or red-visible dyes as termed herein, which are used to a major extent in non-fluorescent formulations, generally do not totally dissolve and even when initially dissolved are subject to precipitation after the mixtures are made. Since red dye penetrants generally have a greater dye content than fluorescent dye penetrants, a serious problem with red penetrants is precipitation of the dye and also deposition of insoluble impurities from the dye in the carrier or solvent.

Accordingly, an object of the present invention is the provision of an improved dye penetrant composition containing dyes which are effective in producing brilliant dye indications from cracks and flaws, but which do not form inactive, undesirable deposits and residues when incorporated into the liquid vehicle of the dye penetrant formulation. A particular object of the invention is the provision of a novel dye penetrant composition containing a highly concentrated liquid single phase red-visible dye composition which immediately and totally enters into solution in the vehicle of the dye penetrant and is essentially free of insolubles, and emits a bright red color. A further object is to provide procedure for dye penetrant inspection of objects, utilizing such dye penetrant composition.

SUMMARY OF THE INVENTION

The above objects and advantages are achieved according to the invention by incorporating into a dye penetrant composition, comprising a nonionic surfactant vehicle as defined hereinafter, particularly an oxyalkylated aliphatic alcohol, a liquid azo dye composition which is soluble or miscible in such surfactant, such azo dye composition consisting essentially of an azo dye containing $C_5$–$C_{12}$ alkyl beta naphthols, or mixtures thereof, as described in greater detail hereinafter. The dye composition is in the form of a single-phase liquid. Particularly effective dye compositions of this type comprise a red-visible azo dye or dyes containing $C_7H_{15}$ beta naphthols. The dye composition also preferably contains a viscosity depressant which serves as a carrier for the dye. Representative dye compositions of the above type are marketed as Automate Red, e.g. Automate Red "B".

It has been found that not only are the above noted single-phase liquid azo dye compositions such as Automate Red "B" free of insolubles, but such dye compositions produce highly stable solutions which when employed in a dye penetrant composition provide brilliant indications of cracks and flaws in the object surface. Since the dyes or dye compositions are in single phase liquid form, the dyes cannot crystallize or precipitate in the dye penetrant composition and these single phase liquid azo dyes produce highly stable solutions which provide brilliant indications in the dye penetrant inspection process. Thus, tests carried out show that the single phase liquid red dyes or dye compositions described herein when employed in dye penetrants produce superior results as compared to commercial red-visible penetrants containing solid dyes in a fluid carrier, in these respects. Further, the single phase liquid red-visible azo dye compositions employed herein are reported to be non-carcinogenic.

The liquid dye penetrant compositions hereof including the unique single phase liquid red visible dye can be formulated as a water washable or solvent removeable dye penetrant composition containing a nonionic water soluble surfactant, or as a post emulsifiable dye penetrant composition containing a nonionic surfactant which is insoluble in water. In the latter case, following application of the dye penetrant composition to the surface of an object to be inspected, an emulsifier composition is then applied to the surface, the emulsified penetrant composition is then removed as by spraying with water, and the surface inspected under suitable white light to obtain the desired indications of cracks and other flaws in the part surface. Alternatively, an organic solvent can be used to remove the dye penetrant.

Thus, there is provided according to the invention a liquid dye penetrant composition for use in non-destructive testing for detecting cracks and other flaws in the surface of an object, comprising a liquid vehicle in the form of a nonionic surfactant, particularly an oxyalkylated aliphatic alcohol, and a liquid azo dye composition which is soluble or miscible in said surfactant, said dye composition consisting essentially of an azo dye or mixtures thereof, containing $C_5$–$C_{12}$ alkyl beta naphthols, and particularly $C_7H_{15}$-beta naphthols. Generally, a liquid organic viscosity depressant compatible with the azo dyes, e.g. xylene, is added to the dye composition, preferably in the proportions noted hereinafter, so that the resulting viscosity of the dye composition is sufficiently low to facilitate handling.

The single phase liquid dye composition in concentrated form and wherein the azo dye is a red visible dye, as defined in greater detail hereinafter, is stable for indefinite periods of time, and hence solid matter does not separate upon long storage and/or at low temperatures.

DETAILED DESCRIPTION OF THE INVENTION

The red-visible dyes employed according to the invention are liquid red azo dyes containing $C_5$–$C_{12}$ alkyl-beta-naphthols. More specifically, such azo dyes contain heptyl-beta-naphthols. Such red dyes have the following formula:

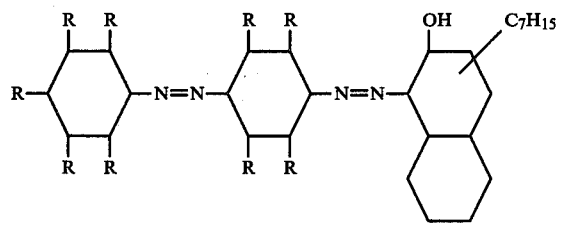

wherein R is either H or $CH_3$.

The red-visible azo dye compositions employed contain about 50–75% by weight of the azo dye or a mixture of azo dyes having the above noted formula, and between about 50–25% by weight of a liquid organic viscosity depressant compatible with the azo dyes. Examples of suitable viscosity depressants employed include aromatic hydrocarbons such as unsubstituted aryl hydrocarbons, e.g. benzene, alkyl-aryl hydrocarbons such as alkyl benzenes, e.g. toluene, xylene and styrene, and alkyl naphthalenes, aliphatic petroleum distillates, such as, for example, kerosene, a naphthenic solvent, phenolic liquids including cresols, "tar acids" and alkylated phenols, chlorinated solvents such as chloroform, ethylene dichloride, perchlorethylene, and chlorobenzenes, alcohols having at least five carbon atoms such as amyl and higher alcohols, unsaturated higher fatty acids such as, for example, oleic acid, ketones such as acetone, methyl ethyl ketone, and methyl isobutyl ketone, and esters such as the alkyl acetates having from 1 to 5 carbon atoms in the alkyl group, for example, ethyl acetate, butyl acetate and amyl acetate. The preferred viscosity depressant is an alkyl-aryl hydrocarbon, particularly xylene.

The viscosity depressant does not serve the function of a solvent per se, but is a carrier for the azo dye proper in which the azo dye is soluble in practically unlimited quantities. The amount of viscosity depressant in the final composition may equal that of the azo dye, but it is preferred that the viscosity depressant be present in a minor amount, e.g., less than 50% by weight. Conversely, the azo dye concentration in the final composition may equal that of the viscosity depressant, but it is preferred that the azo dye be present in a major amount, e.g. more than 50% by weight. Typical dye compositions can contain, for example, 25% of viscosity depressent by weight.

Preferred red-visible dye compositions employed according to the invention contain azo dyes having the above structural formula and are marketed as Automate Red "B" and Automate Fluid Red 13, by Morton International, Inc. The distinction between the different two red dyes employed in such compositions is in the number and distribution of the methyl groups in the substituted amino-azo-benzene radical of the above formula. Such commercially available compositions are understood to contain between about 50 and about 25% of such azo dyes and about 25 to about 50% xylene, by weight.

The above noted dye composition is a homogeneous single phase fluid, which flows readily, and hence the term "liquid" as applied to such dye composition does not refer to a two-phase suspension or emulsion of finely divided solid dye in a fluid carrier, but such dye composition consists of a clear single-phase liquid.

The above azo dye compositions are in concentrated liquid form. In addition to being free of any precipitants or insolubles, such dye compositions have at least 40% of the color value of the solids, e.g. red dyes presently used, and provide a brilliant red coloration when viewed under ordinary white light. The stability of color value is comparable to that of solid red dyes and the dye compositions hereof have high solubility and miscibility with a variety of organic liquids including petroleum hydrocarbons. Thus, dye penetrants employing the above noted liquid azo single phase red dye compositions can also include hydrocarbon extenders as described in greater detail hereinafter.

The above azo dye compositions and their properties are disclosed in U.S. Pat. No. 3,690,809, and such disclosure is incorporated herein by reference.

The nonionic surfactant or carrier of the dye penetrant composition and which is employed as the vehicle for the above liquid single phase azo dye compositions according to the invention, includes any preferably water soluble nonionic surfactants of low viscosity, which are compatible with the red-visible azo dye compositions, and which are compatible with metals, particularly those employed in the aircraft industry, including titanium and nickel alloys. Such nonionic surfactant must be capable of penetrating minute cracks and other defects in the surface of an object to carry a film of dye penetrant composition into such cracks and other surface defects, and remain entrapped in such defects so as to reveal such cracks and other defects due to the dye contained in the composition.

Suitable nonionic surfactant vehicles for the dye penetrant compositions of the invention include oxyalkylated aliphatic alcohols, alkoxylated alkyl phenols and alkyl aryl polyether alcohols, and mixtures thereof. Thus, a preferred class of nonionic surfactants employed in the dye penetrant compositions of the invention are the oxyalkylated aliphatic alcohols which can be prepared by the reaction of an organic compound having a reactive hydrogen atom, such as an aliphatic alcohol, with ethylene oxide, propylene oxide, or mixtures thereof. Such surfactants are biodegradable.

Thus, the latter preferred class of nonionic surfactants consist essentially of an oxyalkylated aliphatic alcohol or mixtures thereof, formed of an aliphatic primary or secondary alcohol carrying ethoxy or propoxy groups, including polyoxyethylene or polyoxypropylene groups, or mixtures thereof.

More particularly, one class of such nonionic solvents or carriers can be defined as straight chain, primary, aliphatic oxyalkylated alcohols, generally in the form of mixtures thereof, wherein the primary aliphatic alcohols can have from 8 to 20 cabon atoms, preferably 10 to 18 carbon atoms, and the oxyalkyl groups are ethylene oxide and propylene oxide, preferably in the form of a mixture thereof.

One group of nonionic carriers within the class of materials defined immediately above is a cogeneric mixture of compounds represented by the formula:

R—O(A)H           (1)

wherein:

R is an essentially linear alkyl group having from 10 to 18 carbon atoms, with the priviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetradecyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The above nonionic surfactants employed as carrier or vehicle for the dye of the penetrant solution according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include for example, that class of surfactants which are marketed as the "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12,75, and the number of propylene oxide groups in such mixture ranges from 1.7 to 7.0, the oxyethylene to oxypropylene ratio in such mixtures being from 1.8:1 to 2.2:1. This mixture of condensation products and the method of their preparation are disclosed in U.S. Pat. No. 3,340,309, and such disclosure is also incorporated herein by reference. The nonionic oxyalkylated alcohols marketed as the "RO-20" grades of "Plurafac", are believed representative of the class of surface active agents disclosed in the latter patent.

Various other "Plurafac" grades which are marketed and are believed to be generally within the above-described classes of oxyalkylated alcohol surfactants are those designated RA-43, A-24, A-25, B-25-5, B-26 and D-25.

Dye penetrant compositions containing the above described primary aliphatic oxyalkylated alcohols as vehicle, and a dye are described in my U.S. Pat. No. 3,915,885.

A class of particularly preferred nonionic biodegradable solvents or carriers which can be employed as substantially the sole vehicle for the dye of the dye penetrant compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed as carrier for the dye penetrant of the invention is a mixture of compounds which can be represented by the formula:

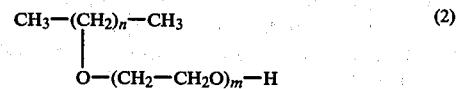

$$CH_3-(CH_2)_n-CH_3 \quad (2)$$
$$|$$
$$O-(CH_2-CH_2O)_m-H$$

where n is in the range from 9 to 13, and m is 3 to 12.

Although preferably each of the above-defined surfactants is formed of a mixture of two or more linear alkyl hydrophobic chains ranging from $C_{11}$ to $C_{15}$, as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

group. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively, as:

| Tergitol | 15-S-3 |
|----------|--------|
| "        | 15-S-5 |
| "        | 15-S-7 |
| "        | 15-S-9 |
| "        | 15-S-12 |

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant of the invention, such as a mixture of the above Tergitols 15-S-5 and 15-S-3; a mixture of 15-S-3 and 15-S-9; and a mixture of 15-S-5 and 15-S-9.

The above preferred class of nonionic biodegradable surfactants employed as carrier or vehicle for the dye of the penetrant solution according to the invention, are prepared by reacting an alcohol or mixture of alcohols, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above nonionic surfactants in the form of ethoxylates of linear secondary aliphatic alcohols, is described in U.s. Pat. No. 2,870,220.

Although Tergitol 15-S-3 is essentially water insoluble and is usually employed in combination with the other members of the Tergitol S series noted above, such as Tergitol 15-S-5, dye penetrant compositions according to the invention containing Tergitol 15-S-3 alone, can be employed. However, Tergitol 15-S-3 has its greatest utility for production of dye penetrants having high sensitivity according to the invention, when employed in combination with the other water washable and water soluble Tergitols such as Tergitol 15-S-5 and Tergitol 15-S-9.

Dye penetrant compositions containing the above described ethoxylates of secondary aliphatic alcohols as vehicle and a dye are described in my U.S. Pat. No. 3,915,886.

Also, particularly effective dye penetrants are provided according to the invention employing a combination or mixture of the above Tergitols 15-S-5 and 15-S-9, and to which there can be added optionally Tergitol 15-S-3, as described in my U.S. Pat. No. 3,939,092.

There can also be employed ethoxylates of linear primary alcohols, corresponding to the ethoxylates of the linear secondary alcohols of the Tergitol S series of nonionic surfactants described above. Thus, the Tergitol 25-L series of nonionic surfactants is derived by ethoxylation of a blend of $C_{12}$ to $C_{15}$ linear primary alcohols, the soluble derivatives of which contain from about 5 to about 7 moles of ethylene oxide.

Other nonionic surfactants which can be employed include alkyl phenols, particularly alkoxylated alkyl phenols such as ethoxylated alkyl phenols, e.g. ethoxylated octyl- or nonyl phenol containing from about 7 to about 15 moles of ethylene oxide per mole of alkyl phenol, which are water soluble. The water insoluble derivatives of such ethoxylated alkyl phenols containing up to 5 moles of ethylene oxide per mole of alkyl phenol can be employed in post emulsifiable dye penetrants of the invention, described in greater detail hereinafter. Also, alkyl aryl polyether alcohols can be employed such as the material marketed as "Triton X-100," which is isooctyl phenyl polyethoxy ethanol.

If desired an extender in the form of an isoparaffinic solvent can be incorporated into the dye penetrant composition of the invention containing a nonionic surfactant of the types exemplified above and the above single phase liquid dye composition, to obtain a low viscosity dye penetrant. Such extender isoparaffinic solvent consists of an isoparaffin having a carbon chain ranging from about 10 to about 17 carbon atoms, and preferably consists essentially entirely of a mixture of isoparaffins having carbon chains ranging from about 10 to about 17 carbon atoms and an average carbon chain ranging from about 12 to about 15, preferably about 13 to about 14, carbon atoms. Thus, the isoparaffinic solvent is practically about 100% of the above isoparaffin or mixture of isoparaffins, and which may contain only a very small amount, e.g. of the order of about 0.1%, normal paraffins. Such isoparaffinic solvent has a number of unique characteristics including low viscosity of the dye penetrants produced therewith, a high flash point, exceptionally high autoignition temperature, very low volatility and absence of odor. Another unique characteristic of the isoparaffinic solvent extender of the invention is that it provides a quick penetration of cracks and other surface defects and a "creeping" or self-developing action in dye penetrants containing such solvent. By "creeping" or "self-developing action" is meant that the dye penetrant which penetrates into the cracks and other defects tends to exude therefrom without the aid of a developer, to provide colored indications of such cracks and other defects.

A representative preferred isoparaffinic solvent particularly having the above chemical and physical characteristics is the solvent marketed as "Isopar M" by Exxon. This solvent is a high boiling narrow-cut isoparaffinic solvent of high purity, having a high flash point of about 175° F. (ASTM D 93), and high autoignition temperature of about 730° F. (ASTM D 286). Such solvent is an isoparaffinic material consisting of a mixture of isoparaffins as above defined, having an average of about 13½ carbon atoms in the isoparaffinic chain, and an average molecular weight of 191, a specific gravity at 60° F. of 0.784, a viscosity at 25° C. of 3.35 cs (ASTM D 445) and a refractive index at 20° C. of 1.4362 (ASTM D 1218). The solvent also has low toxicity including a very low level of skin irritants and a very low concentraton, limited to a few ppm, of trace impurities such as sulfur, chlorine, acids, and carbonyls.

Dye penetrant compositions containing a nonionic surfactant and such isoparaffinic solvent extender are disclosed and claimed in my copending application Ser. No. 925,497, filed July 17, 1978.

The amount of red-visible dye composition which is incorporated into the nonionic, e.g. oxyalkylated alcohol, surfactant or carrier to produce the dye penetrant composition of the invention, can range from about 1 part of the dye composition, to about 2 to about 50, preferably about 4 to about 20, parts of such nonionic surfactant, by volume. In preparing the dye penetrant composition employed according to the invention, the single phase liquid dye composition, e.g. Automate Red B, preferably is added to the nonionic surfactant carrier, in the desired proportion, and the components are thoroughly mixed. If desired, the above isoparaffinic solvent can then be added.

The amount of isoparaffinic solvent extender which can be added to the dye penetrant constitutes a substantial, and usually a major proportion, of the resulting solution, such solvent preferably being present in at least equal volumetric proportions with respect to the nonionic surfactant. Generally, the dye penetrant including the above nonionic surfactant and dye composition is diluted with such solvent in a proportion ranging from about 0.5 to about 15, preferably about 1 to about 7, parts of the isoparaffinic solvent to 1 part of dye penetrant, consisting of the sum of the other components, that is nonionic surfactants, and dye composition, by volume.

Typical dye penetrant compositions containing the liquid single phase red-visible dye composition according to the invention are as follows:

FORMULATION NO. 1:
Biodegradable Red-Visible Penetrant, Water and Solvent Removable

| Components | Parts by Volume |
| --- | --- |
| Automate Red B (dye) | 1 |
| Surfactant Stock (Tergitol 15-S-5 (75%) and Tergitol 15-S-9 (25%) by volume) | 14 |

FORMULATION NO. 2:
Low Viscosity Red-Visible Penetrant, Water and Solvent Removable

| Components | Parts by Volume |
| --- | --- |
| Automate Red B (dye) | 1 |
| Tergitol 15-S-9 (surfactant) | 3 |
| Exxon Isopar M Solvent (extender) | 8 |

The metal surfaces to which the dye penetrant compositions can be applied include a wide variety of metals and alloys and particularly those generally used in the aircraft industry, such as aluminum, copper, titanium, nickel, and their alloys, e.g. chromium plated brass, steel alloys such as PH14-8 Mo, the stainless series of steels, and the like.

If desired, a developer composition can be employed in conjunction with the dye penetrant composition of the invention. When employed, a dry powder or non-aqueous (volatile solvent base) developer composition can be utilized. In each case, the developer composition contains a light colored powder, forming a coating which contrasts with the color of the dye in the penetrant and which acts as a wick or blotter, and causes liquid penetrant containing the dye, i.e. liquid azo dye, which was retained in the cracks or other surface flaws, to be drawn up out of such surface defects by capillary action and to "bleed" through the powder. Exemplary developer compositions for use in conjunction with the dye penetrant composition according to the invention, are those described in my U.S. Pat. No. 4,069,419, which is a dry powder developer consisting of fumed silica and talc, in my U.S. Pat. No. 3,748,469, which is a wet non-aqueous developer composition consisting essentially of isopropyl alcohol, talc and glycol monobutyl ether, and in my copending application Ser. No. 939,550, Sept. 5, 1978, for Wet Nonaqueous Developer Composition, also a wet non-aqueous developer comprising a liquid organic vehicle such as isopropyl alcohol, a developer powder such as talc, and a small amount of a nonionic surfactant, preferably an oxyalkylated alcohol surfactant of the types described above, e.g. Tergitol 15-S-9. The description of such developer compositions contained in the above patents and copending application are incorporated herein by reference.

The dye penetrant compositions employed according to the invention, utilizing the above azo dye composition and nonionic surfactants can be tailored to have varying degrees of sensitivity for detection of the smallest microcracks to gross cracks in a part surface by generally varying the amount of dye composition incorporated, and also by selecting particular surfactants or combinations thereof.

In the method for detecting cracks and other flaws in the surface of an object employing the dye penetrant composition of the invention containing the above single phase liquid azo dye composition, such dye penetrant is applied to the part surface in any suitable manner, as by spraying. The low viscosity penetrant quickly penetrates surface defects such as the cracks in the part surface, and immediately after application of the dye penetrant to the surface of the test part, the excess dye penetrant composition is readily removed from the object surface by water washing, e.g. by application of a water spray or a sprayed mixture of air and water, or by wiping with a water moistened cloth. The dye penetrant compositions hereof, particularly these containing the above Tergitols 15-S-5 to 15-S-9, generally have excellent wetability and practically instantaneous washability with water without removing dye penetrant from the cracks and defects on the part surface, followed by drying the part surface. Such dye penetrant compositions can also be removed from the part surface by means, for example, of an organic solvent such as an alcohol, e.g. isopropyl alcohol, a ketone such as methyl ethyl ketone, or a chlorinated hydrocarbon such as trichloroethane.

As previously noted, if desired, following removal of excess penetrant, a developer composition, e.g. of the types noted above, can then be applied to the part surface followed by removal of any excess developer powder, as by means of an air blast. The part is then viewed under suitable lighting conditions, namely white or ordinary illumination to disclose the penetrant indications from the red-visible dye compositions. Particularly where a wet nonaqueous developer is employed, any remaining developer coating is then removed.

Where it is desired to employ a relatively insoluble nonionic surfactant in the dye penetrant composition, such a Tergitol 15-S-3 noted above, the post emulsifiable dye penetrant inspection method of my U.S. Pat. No. 3,981,185 can be employed. According to such procedure, a post emulsifiable dye penetrant composition containing the nonionic surfactant, e.g. the oxyalkylated alcohol nonionic surfactant, such as Tergitol 15-S-3 as carrier, and the single phase liquid red-visible dye composition hereof, and which can be diluted with a fast drying solvent such as the above isoparaffinic solvent, can be applied as by dipping or spraying, preferably the latter to a test part, and the solvent evaporated, e.g. in about 1 to 2 minutes, followed by treatment of the penetrant covered part as by spraying or dipping, with an emulsifier containing as an essential component water soluble nonionic surfactants, e.g. nonionic surfactants of the same general class as employed as carrier for the dye in the dye penetrant composition, but having water solubility, such as Tergitol 15-S-9, or a combination of Tergitols 15-S-3 and 15-S-12. Water can also be added to the emulsifier as a diluent and in the interest of economy. In such postemulsifiable process, the dye penetrant can contain an oxyalkylated alcohol nonionic surfactant according to formula (2) above, having an average value for m in such formula of about 3 to 4, and the oxyalkylated alcohol nonionic surfactant in the emulsifier can have an average value for m of about 5 to 12.

After a dwell time of about 1 to 5 minutes, the resulting emulsified penetrant is then removed from the surface of the part as by spraying with water, without dislodging the dye penetrant from the surface cracks and thus entrapping the penetrant therein, and the part surface is then dried and inspected under suitable light, i.e. ordinary light. If desired, a developer also can be employed following removal of the emulsified penetrant from the part surface.

Instead of employing a water removable emulsifier followed by a water wash, the above postemulsifiable compositions can be removed by application of an organic solvent.

The following are examples of typical post emulsifiable dye penetrant compositions according to the invention.

FORMULATION NO. 3:
Biodegradable Postemulsifiable and Solvent Removable Red-Visible Penetrant

| Components | Parts by Volume |
| --- | --- |
| Automate Red B (dye) | 1 |
| Tergitol 15-S-3 (surfactant) | 7 |

FORMULATION NO. 4 and No. 5:
Low Viscosity Postemulsifiable and Solvent Removable Red-Visible Penetrants

| Components | Formulation No. 4 High Sensitivity Parts by Volume | Formulation No. 5 Standard Sensitivity Parts by Volume |
| --- | --- | --- |
| Automate Red B (dye) | 3 | 1 |
| Tergitol 15-S-3 (surfactant) | 3 | 3 |
| Exxon Isopar M Solvent (extender) | 8 | 8 |

The postemulsifiable dye penetrant formulations 3, 4 and 5 above can be employed in conjunction with the water reducible or removeable emulsifier formulation No. 6 below.

FORMULAION NO. 6:
Biodegradable and Water Reducible Emulsifier

| Components | Parts by Volume |
| --- | --- |
| Tergitol 15-S-3 (surfactant) | 15 |
| Tergitol 15-S-12 (surfactant) | 50 |
| Water (distilled) | 390 |

Alternatively to the use of the emulsifier formulation No. 6, the post emulsifiable formulations 3, 4 and 5 can be removed using an organic solvent such as isopropyl alcohol or 1,1,1-trichloroethane.

The following are examples of practice of the invention.

EXAMPLE 1

The dye penetrant formulation 1 above was applied as by spraying, to one-half of the surface of a cracked aluminum test panel containing minute cracks of the order of 0.001" to 0.0001" in width, closely distributed over the entire surface. After about two minutes dwell time, a water wash was then applied as by an air-water spray over the coating of the dye penetrant formulation 1 on the test panel, causing instantaneous washing away of the dye penetrant on the surface of the panel without dislodging the dye penetrant from the surface cracks and thus entrapping the penetrant therein.

The other half of the test panel surface was sprayed with a standard commercially available red-visible dye penetrant. A water wash was then applied by an air-water spray over the coating of the standard dye penetrant to wash away excess dye penetrant from the surface of the panel.

Both halves of the test panel surface to which the dye penetrant formulation 1 above and the standard commercial dye penetrant were initially respectively applied, were then covered with the wet nonaqueous developer below, and disclosed in my above copending application, by spraying.

| Components | Parts by Weight |
| --- | --- |
| Tergitol 15-S-9 | 1.0 |
| Isopropyl alcohol | 82.0 |
| Talc | 17.0 |

The above developer was permitted to dwell over the two half surfaces of the test panel for a period of about 2 minutes, until a substantially dry developer coating was formed on both half surfaces of the test panel.

The panel was then placed under ordinary white light and the respective half surfaces viewed in such illumination. It was observed that the first half side of the panel which was initially treated with dye penetrant formulation 1 according to the invention, emitted brilliant red indications superior in brightness and sensitivity to the red-visible indications from the microcracks on the half side of the panel which had been initially treated with the standard commercial red-visible penetrant.

After visual inspection, the developer coatings were removed by water spraying.

EXAMPLE 2

The procedure of Example 1 was followed except that in place of the Automate Red "B" employed in dye penetrant composition 1 of Example 1, the same amount of Automate Fluid Red 13 was employed.

Results similar to the results of Example 1 were obtained.

EXAMPLE 3

Tests on aluminum panels containing microcracks were carried out employing procedure similar to that employed in Example 1, utilizing dye penetrant formulation 2 above on one-half of the surface of the test panel and utilizing the standard commercial red-visible dye penetrant on the other half of the panel.

Results obtained were similar to those obtained in Example 1, except that the brilliance and sensitivity and concentration of cracks revealed on that side of the panel treated with the dye penetrant formulation 2 were not as great as in the case of formulation 1 of Example 1, but were still equal to or superior in these respects to the side of the panel treated with the standard commercial red-visible penetrant.

EXAMPLE 4

The post emulsifiable red-visible penetrant formulation 3 above was applied as by spraying to one-half of the surface of an aluminum test panel containing microcracks.

The other half of the test panel surface was sprayed with a standard commercial red-visible post emulsifiable dye penetrant composition.

The dye penetrant covered surfaces on both halves of the test panel were then sprayed with the above emulsifier formulation 6 the emulsifier being allowed to dwell on the initially applied penetrant for about 2 minutes, and thereafter a spray of water was used to remove the emulsifier-penetrant blend on each half of the panel.

Both halves of the test panel were than covered with the wet nonaqueous developer of Example 1 above and allowed to dwell thereon for a period of about 2 minutes, to form dry developer coatings.

The panel was then placed under white light illumination and the above treated surfaces on both halves of the panel viewed in such illumination. The sharpness and brilliance of the red colored indications on the first half of the panel to which the post emulsifiable penetrant formulation 3 was applied were superior in these respects to the other half of the panel to which the standard red-visible post emulsifiable penetrant was applied.

EXAMPLE 5

The procedure of Example 4 was followed except that the first half of the panel was treated initially with the high sensitivity low viscosity red-visible post emulsifiable dye penetrant formulation 4 above, and the other half of the panel was treated with a corresponding high sensitivity commercial red-visible post emulsifiable dye penetrant formulation.

Both halves of the test panel, following application of emulsifier formulations 6, and removal of the resulting emulsifier-penetrant blends were viewed in visible light, revealing visual brilliant red traces of crack indications on that side of the panel treated with formulation 4, which were superior in brightness and intensity to the red colored crack indications emitted from the other side of the panel treated with the commercial red-visible post emulsifiable penetrant.

EXAMPLE 6

The procedure of Example 4 was followed except that the first half of the panel was treated initially with the red-visible standard sensitivity post-emulsifiable dye penetrant formulation 5 above, and the other half of the panel was treated with a standard commercial red-visible standard sensitivity post emulsifiable dye penetrant.

Results similar to those of Example 4 were obtained.

The excess of the water washable dye penetrants of the invention, e.g., formulations 1 and 2 of Examples 1 and 3, and of the post emulsifiable dye penetrant compositions of the invention, e.g. formulations 3 to 5 of Examples 4 to 6, also can be removed from the part surface by washing with isopropyl alcohol or trichlorothane instead of by use of an emulsifier followed by a water wash.

It was observed that the dye penetrant formulations 1 to 5 containing the red-visible single phase liquid azo dye composition of the invention, remained stable without precipitation or formation of insolubles, over extended periods of time.

From the foregoing, it is seen that the invention provides an improved effective water washable or solvent removable red-visible dye penetrant composition or post emulsifiable dye penetrant composition consisting essentially of a nonionic surfactant and a single-phase liquid dye composition consisting essentially of certain liquid red azo dyes in concentrated form, and which are not solutions of dry dyes, and from which solid matter does not separate. Application of such dye penetrant compositions to a part surface for detection of cracks therein results in efficiently and quickly obtaining brilliant red visible light indications of cracks in the part surface, generally superior in brilliance and sensitivity to prior art commercial red dye penetrants containing solid dyes in solution.

Since various changes and modifications of the invention will occur to and can be made readily by those skilled in the art without departing from the invention concept, the invention is not to be taken as limited except by the scope of the appended claims.

I claim:

1. A method for detecting cracks and other defects in the surface of an object which comprises applying to said surface a liquid dye penetrant composition comprising a nonionic surfactant, and a liquid azo dye composition which is soluble or miscible in said surfactant, said dye composition consisting essentially of an azo dye containing $C_5$–$C_{12}$ alkyl beta naphthols, or mixtures thereof, said dye composition being a single-phase liquid, removing excess dye penetrant composition from said cracks and defects in said surface, and viewing the surface of said object under lighting conditions to obtain colored traces from the dye in said cracks and other defects.

2. The method as defined in claim 1, said azo dye being a red-visible dye containing $C_7H_{15}$ beta naphthols, said dye composition containing a liquid organic viscosity depressant compatible with said azo dye, in an amount from about 25 to about 50% by weight of said viscosity depressant, said azo dye being present in an amount of about 50 to about 75% by weight, employing about 1 part of said azo dye composition to about 2 to about 50 parts of said surfactant, by volume.

3. The method as defined in claim 2, said azo dye being a red azo dye having the formula:

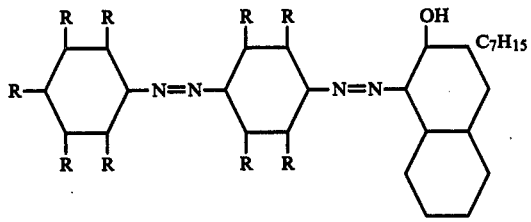

wherein R is H or $CH_3$.

4. The method as defined in claim 3, said nonionic surfactant being an oxyalkylated aliphatic alcohol or mixtures thereof, formed of an aliphatic primary or secondary alcohol carrying ethoxy or propoxy groups, or mixtures thereof.

5. The method as defined in claim 4, said dye penetrant composition containing as extender an isoparaffinic solvent consisting of as isoparaffin having a carbon chain ranging from about 10 to about 17 carbon atoms, and an average carbon chain ranging from about 12 to about 15 carbon atoms, said isoparaffinic solvent being present in an amount ranging from about 0.5 to 15 parts, to 1 part of the sum of said surfactant and said dye composition, by volume.

6. The method as defined in claim 3, wherein said surfactant consists of ethoxylates of a mixture of alcohols having the formula:

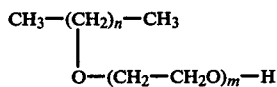

wherein n is in the range of from 9 to 13 and m is an average of 3 to 12.

7. The method as defined in claim 6, said liquid viscosity depressant being an alkyl-aryl hydrocarbon.

8. The method as defined in claim 7, said liquid viscosity depressant being xylene, employing about 1 part of said azo dye composition to about 4 to about 20 parts of said surfactant, by volume.

9. The method as defined in claim 3, said dye penetrant composition being a post emulsifiable dye penetrant composition wherein said surfactant in said post emulsifiable dye penetrant composition has limited water solubility, including contacting the dye penetrant covered surface after application of said post emulsifiable dye penetrant composition, with an emulsifier containing as essential component a second nonionic surfactant as above defined, said second surfactant being essentially water soluble, and contacting the emulsified penetrant on the surface of said object with water for removing said emulsified dye penetrant from the surface of said object, and drying said surface prior to said viewing said object.

10. The method as defined in claim 9, said liquid viscosity depressant being an alkyl substituted aryl hydrocarbon, and wherein said surfactant in both said dye penetrant composition and said emulsifier consists of ethoxylates of a mixture of alcohols having the formula:

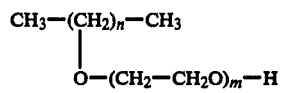

where n is in the ranges of from 9 to 13 and m is an average of 3 to 12.

11. The method as defined in claim 10, said liquid viscosity depressant being xylene, employing about 1 part of said azo dye composition to about 4 to about 20 parts of said surfactant, by volume.

12. The method as defined in claim 10, said dye penetrant composition containing as extender a substantial portion of an isoparaffinic solvent consisting of an isoparaffin having a carbon chain ranging from about 10 to about 17 carbon atoms, and an average carbon chain ranging from about 12 to about 15 carbon atoms.

13. The method as defined in claim 2, said excess dye penetrant composition being removed by water or solvent wash.

14. The method as defined in claim 1, including applying a developer to said surface after removing said excess dye penetrant composition from said surface, and prior to said viewing the surface of said object.

15. A liquid dye penetrant composition for use in nondestructive testing for detecting cracks and other defects in the surface of an object, comprising a nonionic surfactant, and a liquid azo dye composition which is soluble or miscible in said surfactant, said azo dye composition consisting essentially of an azo dye containing $C_5-C_{12}$ alkyl beta naphthols, or mixtures thereof, said azo dye composition being a singe-phase liquid.

16. The dye penetrant composition as defined in claim 15, said azo dye being a red-visible azo dye containing $C_7H_{15}$ beta naphthols.

17. The dye penetrant composition as defined in claim 16, said dye composition containing a liquid organic viscosity depressant compatible with said azo dye, in an amount from about 25 to about 50% by weight of said viscosity depressant, said azo dye being present in an amount of about 50 to about 75% by weight, employing about 1 part of said azo dye composition to about 2 to about 50 parts of said surfactant, by volume.

18. The dye penetrant composition as defined in claim 17, said nonionic surfactant being selected from the group consisting of oxyalkylated aliphatic alcohols, alkoxylated alkyl phenols and alkyl aryl polyether alcohols, and mixtures thereof.

19. The dye penetrant composition as defined in claim 17, said nonionic surfactant being an oxyalkylated aliphatic alcohol or mixtures thereof, formed of an aliphatic primary or secondary alcohol carrying ethoxy or propoxy groups, or mixtures thereof, employing about 1 part of said azo dye composition to about 4 to about 20 parts of said surfactant by volume, said dye penetrant composition being substantially free of insolubles.

20. The dye penetrant composition as defined in claim 16, said dye penetrant composition containing as extender a substantial portion of an isoparaffinic solvent consisting of an isoparaffin having a carbon chain ranging from about 10 to about 17 carbon atoms, and an average carbon chain ranging from about 12 to about 15 carbon atoms.

21. A liquid dye penetrant composition for use in nondestructive testing for detecting cracks and other defects in the surface of an object, comprising a nonionic surfactant and a red visible single-phase liquid azo dye composition consisting essentially of a red azo dye having the formula:

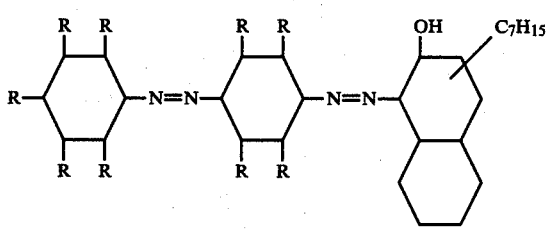

wherein R is H or $CH_3$.

22. The dye penetrant composition as defined in claim 21, said dye composition containing a liquid organic viscosity depressant compatible with said azo dye, in an amount from about 25 to about 50% by weight of said viscosity depressant, said azo dye being present in an amount of about 50 to about 75% by weight.

23. The dye penetrant composition as defined in claim 22, employing about 1 part of said azo dye composition to about 2 to about 50 parts of said surfactant, by volume.

24. The dye penetrant composition as defined in claim 23, said nonionic surfactant being an oxyalkylated aliphatic alcohol or mixtures thereof, formed of an aliphatic primary or secondary alcohol carrying ethoxy or propoxy groups, or mixtures thereof, employing about 1 part of said azo dye composition to about 4 to about 20 parts of said surfactant by volume, said dye penetrant composition being substantially free of insolubles.

25. The dye penetrant composition as defined in claim 24, said liquid viscosity depressant being an alkyl-aryl hydrocarbon.

26. The dye penetrant composition as defined in claim 24, said liquid viscosity depressant being xylene.

27. The dye penetrant composition as defined in claim 23, said liquid viscosity depressant being selected from the group consisting of unsubstituted and alkyl substituted aryl hydrocarbons, aliphatic petroleum distillates, phenolic liquids, chlorinated solvents, alcohols having at least five carbon atoms, unsaturated higher fatty acids, ketones selected from the group consisting of acetone, methyl ethyl ketone and methyl isobutyl ketone, and an ester selected from the group consisting of alkyl acetates having from 1 to 5 carbon atoms in the alkyl group.

28. The dye penetrant composition as defined in claim 27, wherein said surfactant consists of ethoxylates of a mixture of alcohols having the formula:

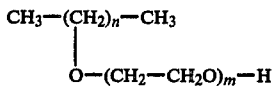

where n is in the range from 9 to 13 and m is an average of 3 to 12.

29. The dye penetrant composition as defined in claim 28, wherein said surfactant is selected from the group consisting of said ethoxylates of said mixture of alcohols, wherein n ranges from 9 to 13, and m is an average of 3, 5, 7, 9, or 12.

30. The dye penetrant composition as defined in claim 28, said dye penetrant composition containing as extender an isoparaffinic solvent having an average carbon chain ranging from about 13 to about 14 carbon atoms, and having a flash point of about 175° F., said isoparaffinic solvent being present in an amount ranging from about 1 to 7 parts, to 1 part of the sum of said surfactant and said dye composition, by volume.

31. The dye penetrant composition as defined in claim 27, wherein said surfactant consists of the ethoxylates of a mixture of $C_{12}$ to $C_{15}$ linear primary alcohols and contains from 5 to 9 moles of ethylene oxide per mole of primary alcohol.

32. The dye penetrant composition as defined in claim 28, employing a combination of said nonionic surfactants wherein m in one of said surfactants is an average of 5 and m in another of said surfactants is an average of 9.

33. The dye penetrant composition as defined in claim 28, said liquid viscosity depressant being xylene, employing about 1 part of said azo dye composition to about 4 to about 20 parts of said surfactant, by volume.

34. The dye penetrant composition as defined in claim 23, said nonionic surfactant being of the group consisting of (a) straight chain, primary, aliphatic oxyalkylated alcohols, wherein said alcohols can contain from 8 to 20 carbon atoms and the oxyalkyl groups are ethylene oxide, propylene oxide, or a mixture of ethylene oxide and propylene oxide groups, and (b) ethoxylates of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide.

35. The dye penetrant composition as defined in claim 34, wherein said surfactant (a) is a mixture of compounds having the formula:

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) are ethoxylates of a mixture of alcohols having the formula:

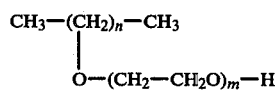

where n is in the range from 9 to 13 and m is an average of 3 to 12.

* * * * *